US010688233B2

(12) United States Patent
Patel et al.

(10) Patent No.: US 10,688,233 B2
(45) Date of Patent: Jun. 23, 2020

(54) METHOD AND SYSTEM FOR THE AUTOMATED PROCESSING OF BIOLOGICAL FLUID DURING LOW LEVEL ALERT CONDITION (71) Applicant: Fenwal, Inc., Lake Zurich, IL (US)

(72) Inventors: Amit J. Patel, Algonquin, IL (US); Samantha M. Planas, Wauconda, IL (US); Melissa A. Thill, Kenosha, WI (US)

(73) Assignee: Fenwal, Inc., Lake Zurich, IL (US)

( * ) Notice: Subject to any disclaimer, the term of this patent is extended or adjusted under 35 U.S.C. 154(b) by 567 days.

(21) Appl. No.: 14/577,456

(22) Filed: Dec. 19, 2014

(65) Prior Publication Data
US 2016/0177264 A1 Jun. 23, 2016

(51) Int. Cl.
A61M 1/34 (2006.01)
A61M 1/16 (2006.01)
A61M 1/36 (2006.01)
A61M 1/26 (2006.01)
C12N 5/078 (2010.01)

(52) U.S. Cl.
CPC .......... A61M 1/1601 (2014.02); A61M 1/262 (2014.02); A61M 1/34 (2013.01); A61M 1/3403 (2014.02); A61M 1/3496 (2013.01); A61M 1/3693 (2013.01); A61M 1/265 (2014.02); A61M 2205/18 (2013.01); C12N 5/0641 (2013.01)

(58) Field of Classification Search
CPC ...... A61M 1/1601; A61M 1/262; A61M 1/34; A61M 1/3496; A61M 1/3693; A61M 2205/18
See application file for complete search history.

(56) References Cited

U.S. PATENT DOCUMENTS

| | | |
|---|---|---|
| 4,718,891 A | 1/1988 | Lipps |
| 5,194,145 A | 3/1993 | Schoendorfer |
| 5,234,608 A | 8/1993 | Duff |
| 5,758,643 A | 6/1998 | Wong et al. |
| 5,941,842 A | 8/1999 | Steele et al. |
| 6,077,443 A | 6/2000 | Goldau |
| 7,029,456 B2 | 4/2006 | Ware et al. |
| 7,169,352 B1 | 1/2007 | Felt et al. |
| 7,513,882 B2 | 4/2009 | Felt et al. |
| 7,647,834 B2 | 1/2010 | O'Mahony et al. |
| 7,699,806 B2 | 4/2010 | Ware et al. |
| 7,780,618 B2 | 8/2010 | Felt et al. |
| 8,088,090 B2 | 1/2012 | Felt et al. |

(Continued)

FOREIGN PATENT DOCUMENTS

| | | |
|---|---|---|
| EP | 0830158 B1 | 3/1998 |
| EP | 1110566 A2 | 6/2001 |

(Continued)

OTHER PUBLICATIONS

Extended European Search Report dated Apr. 25, 2016 for European Patent Application No. 15200469.3-1651.

Primary Examiner — Leslie R Deak
(74) Attorney, Agent, or Firm — Cook Alex Ltd.

(57) ABSTRACT

Methods and systems for processing biological fluid are disclosed. The methods and systems allow for processing of biological fluid to continue in the event that certain non-operator-correctable hardware errors of a non-critical nature are detected during such processing.

18 Claims, 7 Drawing Sheets (56) References Cited

U.S. PATENT DOCUMENTS

| | | | |
|---|---|---|---|
| 8,608,658 B2 | 12/2013 | Burbank et al. | |
| 8,617,093 B2 | 12/2013 | Kopperschmidt et al. | |
| 8,641,615 B2 | 2/2014 | Burbank et al. | |
| 8,728,020 B2 | 5/2014 | Caleffi et al. | |
| 9,381,291 B2 | 7/2016 | Boggs et al. | |
| 2002/0016568 A1* | 2/2002 | Lebel | A61N 1/37211 604/131 |
| 2008/0154197 A1 | 6/2008 | Derrico et al. | |
| 2009/0292236 A1 | 11/2009 | Kleinekofort | |
| 2011/0071465 A1* | 3/2011 | Wang | A61M 1/28 604/67 |
| 2013/0184638 A1 | 7/2013 | Scarpaci et al. | |
| 2013/0204174 A1 | 8/2013 | Olde et al. | |
| 2013/0233798 A1 | 9/2013 | Wiktor et al. | |
| 2014/0074008 A1 | 3/2014 | Fontanazzi et al. | |
| 2014/0088483 A1 | 3/2014 | Fontanazzi et al. | |
| 2014/0358061 A1 | 12/2014 | Cappella et al. | |
| 2015/0027936 A1 | 1/2015 | Kelly et al. | |
| 2015/0182682 A1* | 7/2015 | Wegener | A61M 1/3496 210/651 |

FOREIGN PATENT DOCUMENTS

| | | |
|---|---|---|
| WO | WO 02/35979 A2 | 5/2002 |
| WO | WO 2013/029786 A1 | 3/2013 |

* cited by examiner

METHOD AND SYSTEM FOR THE AUTOMATED PROCESSING OF BIOLOGICAL FLUID DURING LOW LEVEL ALERT CONDITION

FIELD OF THE DISCLOSURE

The present disclosure is directed to methods and systems for processing biological fluid. More particularly, the present invention is directed to such methods and systems utilizing a reusable hardware component that includes a pre-programmed controller and a disposable fluid processing circuit mountable on the hardware component. The controller is capable of distinguishing between and among hardware errors of varying types and significance and allows for processing of biological fluid to continue in the event of certain non-operator-correctable hardware errors of a non-critical nature.

BACKGROUND

The various blood processing systems now make it possible to collect and/or process particular blood constituents, instead of whole blood, from a blood source such as, but not limited to, a container of previously collected blood or other living or non-living source. Typically, in such systems, whole blood is drawn from a blood source, a particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into one or more of its constituents (e.g., red cells, platelets, and plasma) by processing through a disposable fluid flow circuit that is associated with a durable, reusable device that controls the processing of fluid through the flow circuit by a variety of pumps, valves, sensors and the like that operate on the fluid flow circuit. Typical separation techniques include centrifugation, such as in the AMICUS® separator from Fenwal, Inc., of Lake Zurich, Ill., or other centrifugal separation devices, or membrane separation such as a spinning membrane-type separator, such as the AUTOPHERESIS-C® and AURORA devices from Fenwal, Inc.

While the above refers to apheresis systems in particular, the present subject matter, as seen below, is not limited to such whole blood apheresis applications but may include systems for processing blood components or other biological fluid components. With reference to apheresis systems, as noted above, blood components that are not collected are typically returned to the source or subject, such as a patient or donor. These may include concentrated red cells, plasma, platelets or some combination of these. Also, it is common to infuse into the donor or patient a replacement fluid, such as saline, to replace the volume of the blood components that have been removed and not returned. To this end, such systems include a fluid flow path that communicates with the source or subject, such as but not limited to a human donor or patient, for directing or returning blood, blood components or other fluids to the subject. The fluid flow path is usually in the form of flexible plastic flow tubing terminating in a needle or other access device that is inserted into a subject's (human donor's or patient's) vein.

Systems of the type described above often include sensors and/or detectors that monitor various aspects of the biological fluid processing procedure as well as system performance and operation. When necessary, in response to a sensed or detected abnormal condition, the system may generate an alarm or an alert informing the operator of the specific condition. Some conditions may require termination of the biological fluid processing procedure. Others may require some form of operator intervention, correction, and/or acknowledgement.

There are, however, still other conditions that cannot be corrected by the operator. For example, certain errors detected in the hardware cannot be corrected by the operator. Examples of such hardware errors include pump and spinner rate errors (e.g., if the spinner is spinning too fast, too slow, is stalled, is not changing rates, is not stopping fast enough, or the direction of spin is reversed); clamps that do not open/close when intended; disturbances on the weight scales that increase signal variation/noise, but do not affect the average reading; inflation of the pressure cuff for a long period of time; readings of the pressure sensors that are outside of the normal range, but not hazardous; analog-to-digital conversions that did not complete as expected. Many such errors are not critical to the performance of the device or the processing of the biological fluid provided that they do not persist beyond a certain threshold and do not pose a threat to the safety of the patient/donor.

Generally, an alert or an alarm requiring operator action, even such as operator acknowledgment of an alarm, adds time to the fluid processing procedure. This can be particularly undesirable where one operator is monitoring several procedures being performed on several devices at the same time such as in a blood center or other facility. Thus, it would be particularly advantageous to provide a system whereby processing can resume even in view of a certain (low) level or category of hardware error without the need for operator intervention, nor acknowledgment, nor a complete termination of the procedure. The methods and systems of the present disclosure are particularly advantageous where the only operator action is to resume the procedure and monitor for recurrence of the same issue. In accordance with the present disclosure, the system can carry out and complete this action automatically and independently of the operator. The subject matter of the present disclosure addresses these and other needs.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto. These and other aspects may be found in the description, drawings, claims and the additional listing of various aspects set forth later in this specification.

In one aspect, the present disclosure is directed to a method of processing a biological fluid in an automated biological fluid processing device including a hardware unit comprising a controller including pre-programmed instructions and a disposable fluid circuit mounted on the hardware unit. The method includes processing a biological fluid; detecting an error of a certain type and category in the hardware unit; pausing the processing; and resuming the processing without operator intervention.

In another aspect, the present disclosure is directed to a system for processing a biological fluid including a reusable hardware unit comprising a controller including pre-programmed instructions to (a) detect errors in the hardware unit (b) recognize errors of varying types in the hardware unit and (c) allow processing of a biological fluid to continue without operator intervention. The system also includes a disposable fluid processing circuit mounted on the hardware unit.

DETAILED DESCRIPTION OF THE EMBODIMENTS

The embodiments disclosed herein are for the purpose of providing an exemplary description of the present subject matter. They are only exemplary, however, and the present subject matter may be embodied in various forms. Therefore, specific details disclosed herein are not to be interpreted as limiting the subject matter as defined in the accompanying claims.

Figure 1:
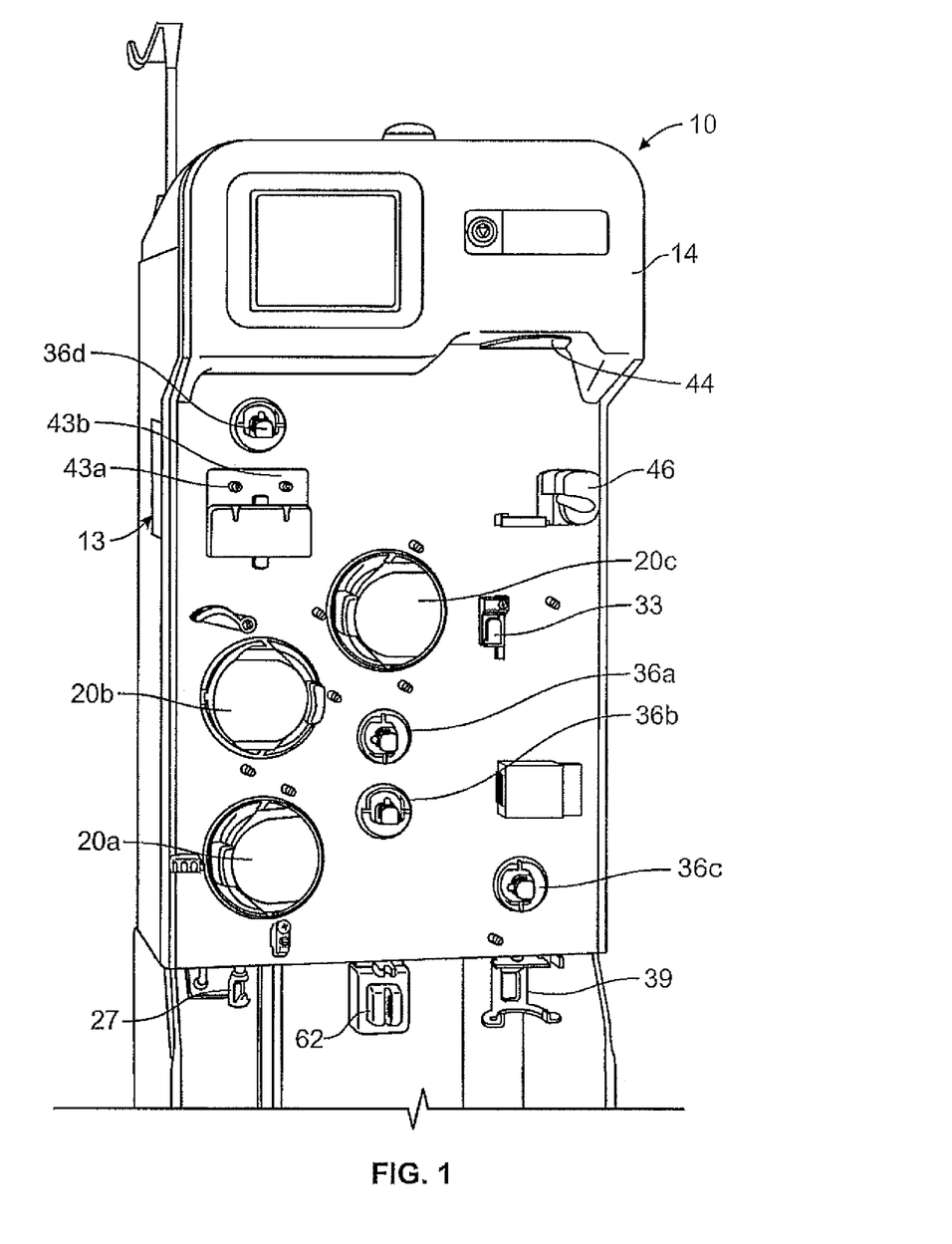
FIG. 1 is a front perspective view of an exemplary biological fluid processing system and, more specifically, a fluid separation system such as an apheresis system according to an aspect of the present disclosure.
Figure 2:
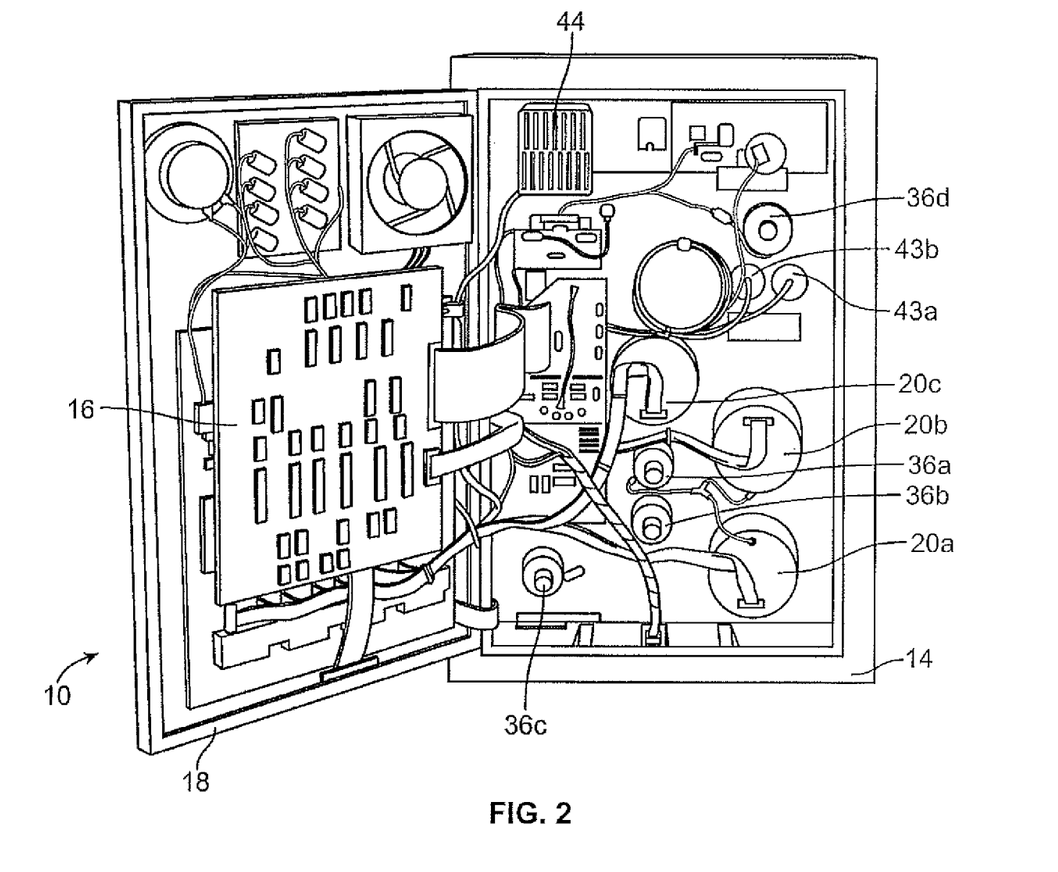
FIG. 2 is a rear perspective view of the fluid separation system of FIG. 1, with a rear door of a cabinet or housing thereof in an open position.
Figure 3:
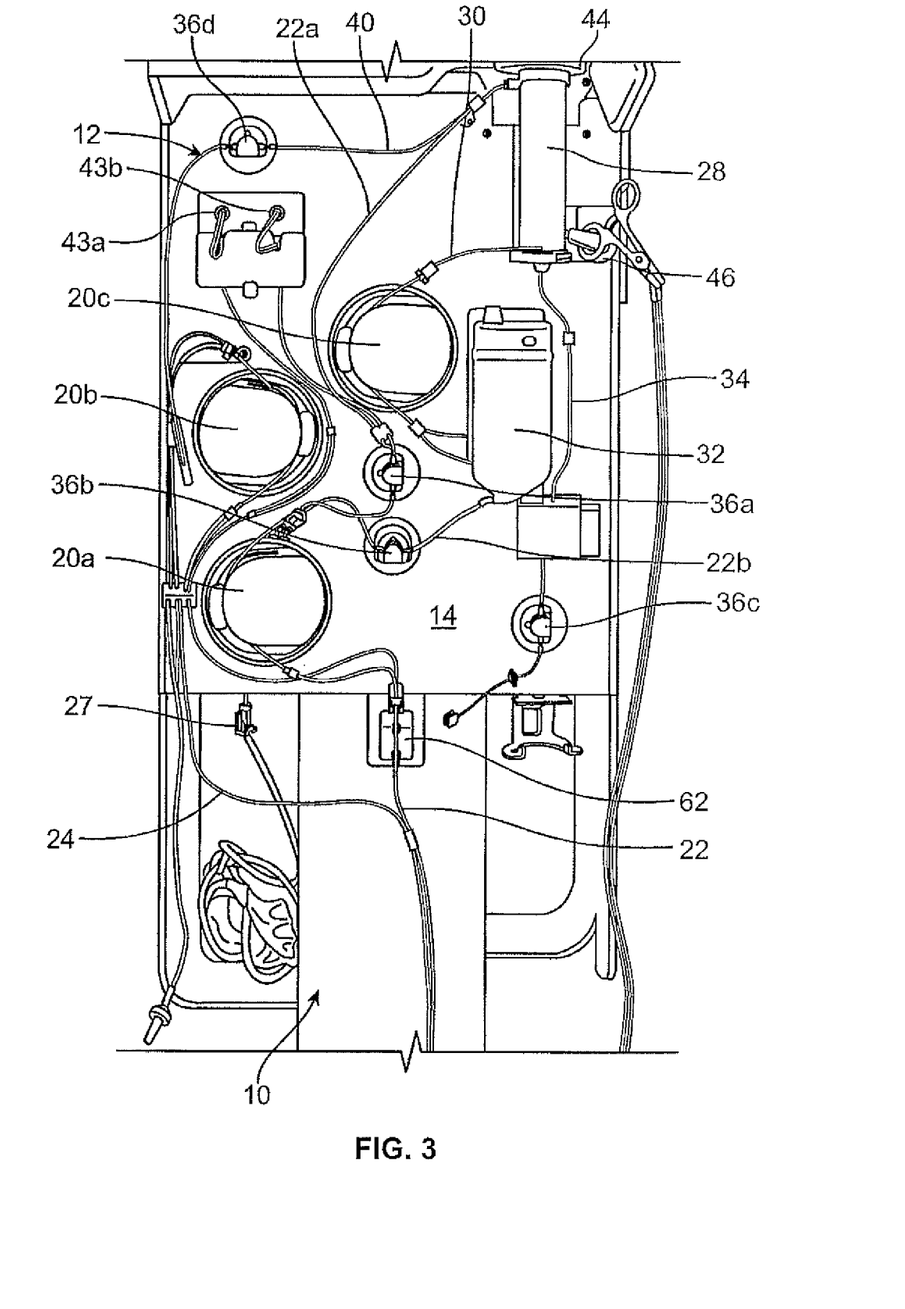
FIG. 3 is a front perspective view of the fluid separation system of FIG. 1, with a fluid flow circuit associated therewith.

The present disclosure is directed to methods and systems for processing a biological fluid such as, but not limited to, blood. According to an aspect of the present disclosure, a durable or reusable hardware unit in combination with a separate fluid processing circuit (which may be disposable) to separate a plasma-containing fluid into separated plasma and a concentrated fluid. FIGS. 1 and 2 illustrate an exemplary fluid separation system 10, while FIG. 3 illustrates an exemplary fluid flow circuit 12 mounted onto the hardware unit 13, but it should be understood that the illustrated fluid separation system 10 and fluid processing circuit 12 are merely exemplary of such systems and circuits and that differently configured fluid processing systems and fluid flow circuits may be provided without departing from the scope of the present disclosure.

The system 10 of FIG. 1 is configured for processing whole blood, but it may be used to process other biological fluids The fluid may come from any fluid source and be returned to any recipient, which may be the same as or different from the fluid source. In one embodiment, the fluid source/recipient is a living donor or patient (e.g., a human blood donor), while in other embodiments the fluid source, subject and/or fluid recipient may be a non-living source/recipient (e.g., a blood bag or other fluid container).

Figure 5:
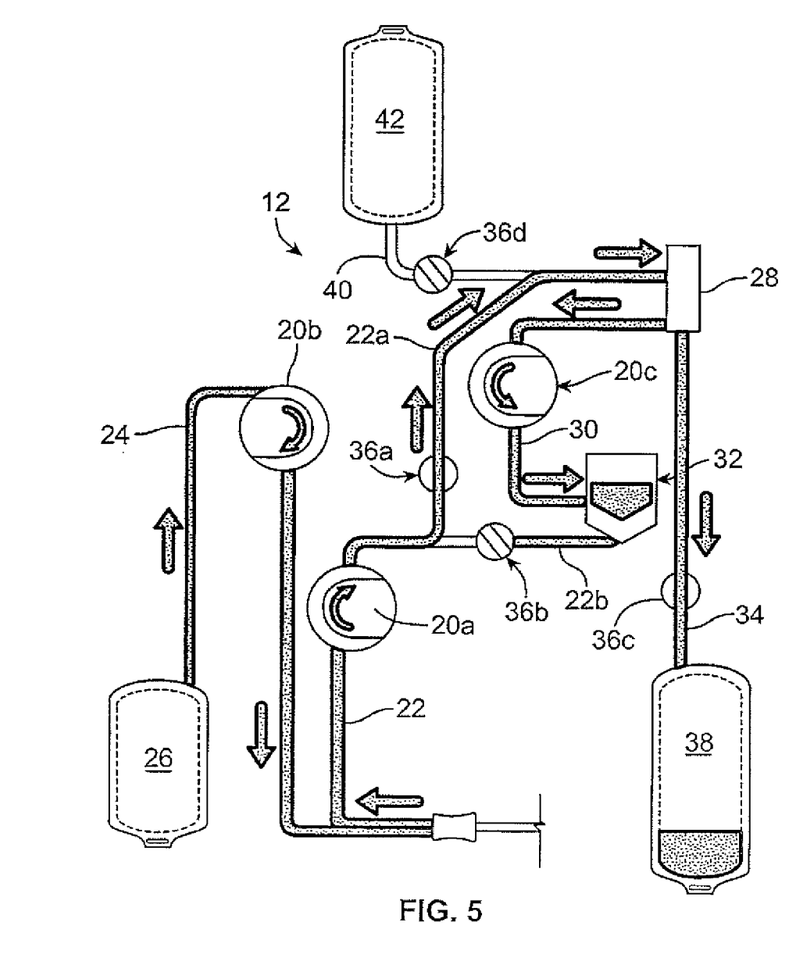
FIG. 5 is a schematic view of the fluid flow circuit and fluid separation system of FIG. 3, in a fluid draw mode.
Figure 6:
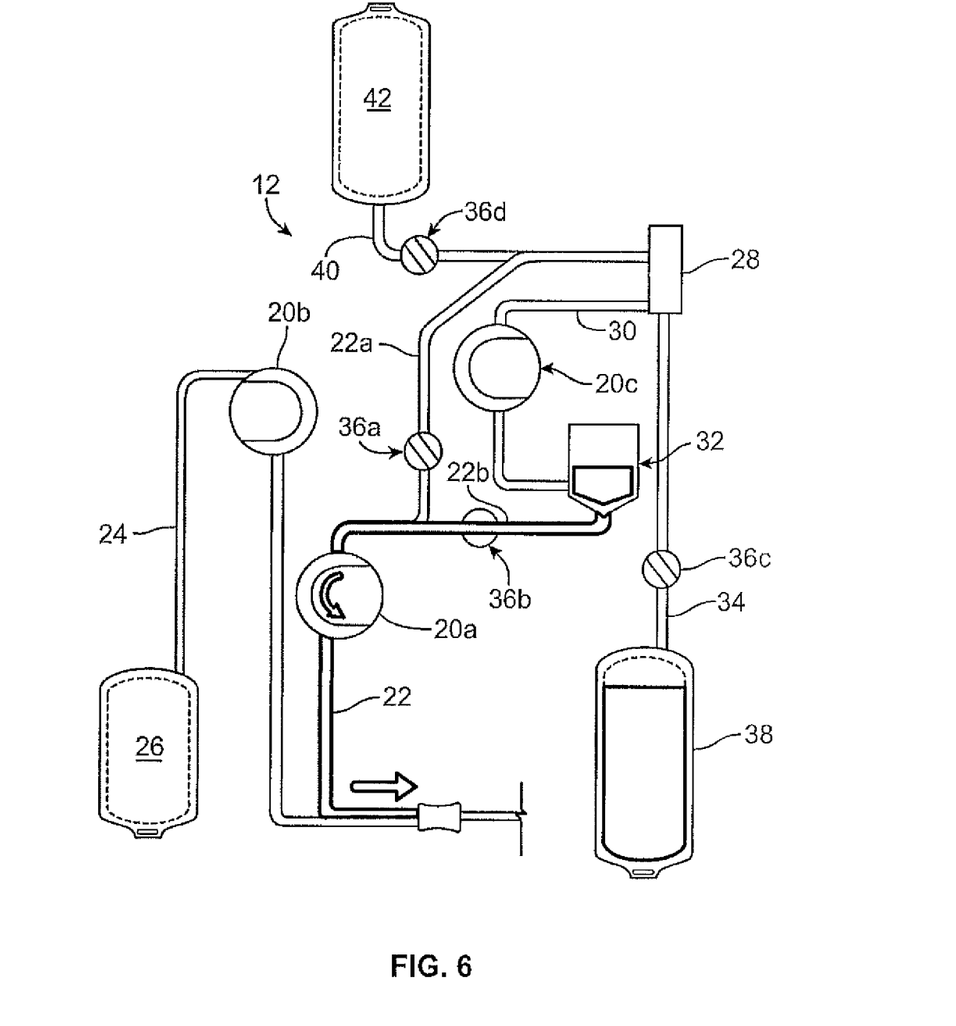
FIG. 6 is a schematic view of the fluid flow circuit and fluid separation system of FIG. 3, in a fluid return mode.

The illustrated system 10 includes the hardware unit 13 shown as a cabinet or housing 14, with several components positioned outside of the cabinet 14 (e.g., associated with a front wall or surface or panel of the cabinet 14) and additional components (including a central processing unit or controller 16, such as programmable micro-processor based controller) and interconnects positioned inside of the cabinet 14, which may be accessed by opening a rear door 18 of the system 10, as shown in FIG. 2. "Controller" is used generally and may include any higher or lower level processors that are part of the overall control or operation of the system or process, whether combined in a single processing unit or separate discrete components or structures. Among the system components positioned on the outside of the cabinet 14, one or more pumps or pump stations 20a-20c may be provided, with the pumps 20a-20c configured to accommodate tubing lines of the fluid flow circuit 12. One of the pumps 20a may be provided as a source/recipient access pump, which may be associated with a source/recipient access or fluid flow path or line 22 of the fluid flow circuit 12 and operates to draw fluid from a fluid source (FIG. 5) and to return fluid to a fluid recipient (FIG. 6). Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. A third pump 20c may be provided as a return fluid pump, which may be associated with a return fluid outlet line 30 and operates to draw a return fluid (i.e., a fluid constituent to be returned or infused into a fluid recipient) from the fluid separation chamber 28 and direct it into a return fluid reservoir 32 after the fluid has been separated into a return fluid and a collection fluid in the fluid separation chamber 28. The fluid return or infusion pump 20c may also be referred to as a red cell pump in the illustrated embodiment, as red cell concentrate may be a typical fluid returned to a donor in a procedure where the primary collection target is plasma.

In the illustrated embodiment, the pumps 20a-20c are rotary peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a collection fluid outlet line 34 of the fluid flow circuit 12 to draw a collection fluid from the fluid separation chamber 28 after the fluid from the fluid source has been separated into a return fluid and a collection fluid. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a return fluid reservoir 32 of the fluid flow circuit 12 to allow (FIG. 6) or prevent (FIG. 5) the flow of return or replacement fluid through the infusion branch 22b. A third clamp or valve 36c may be provided as a collection fluid clamp or valve, which may be associated with the collection fluid outlet line 34 to allow (FIG. 5) or prevent (FIG. 6) the flow of collection fluid through the collection fluid outlet line 34 and into a collection fluid container 38. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b of conventional design that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid (for example whole blood) from a fluid source and/or directs processed or replacement fluid (for example blood components, such as red cell concentrate, and/or saline) to a fluid recipient or subject, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. as described in more detail later, if the controller 16 determines that an undesired or improper pressure is present within the fluid flow circuit 12 (e.g., a high pressure due to an occlusion of one of the tubing lines), then the controller 16 may generate an alarm and/or instruct one or more of the pumps 20a-20c and/or one or more of the clamps or valves 36a-36d to act so as to alleviate the improper pressure condition (e.g., by changing the fluid flow rate, reversing the direction of operation of one of the pumps 20a-20c and/or opening or closing one of the clamps or valves 36a-36d). Additional or alternative pressure sensors may also be provided without departing from the scope of the present disclosure.

As shown in FIG. 1, the system 10, and more specifically, hardware unit 13 may also include a separation actuator 44 that interacts with a portion of the fluid separation chamber 28 to operate the fluid separation chamber or separator 28.

A chamber lock 46 may also be provided to hold the fluid separation chamber or separator 28 in place with respect to the system cabinet 14 and in engagement with the separation actuator 44. The configuration and operation of the separation actuator 44 depends upon the configuration of the fluid separator 28. In the illustrated embodiment, the fluid separator 28 is provided as a spinning membrane-type separator, such as a separator of the type described in greater detail in U.S. Pat. Nos. 5,194,145 and 5,234,608 or in PCT Patent Application Publication No. WO 2012/125457 A1, all of which are hereby incorporated herein by reference. If provided as a spinning membrane-type separator, the fluid separation chamber 28 may include a tubular housing 48 (FIG. 4), with a microporous membrane 50 positioned therein. An inlet 52 allows a fluid from a fluid source to enter into the housing 48 (via the draw branch 22a of the source/recipient access line 22), while a side outlet 54 allows return fluid to exit the housing 48 (via the return fluid outlet line 30) and a bottom outlet 56 allows collection fluid to exit the housing 48 (via the collection fluid outlet line 34) after the fluid from the fluid source has been separated into return fluid and collection fluid.

Figure 4:
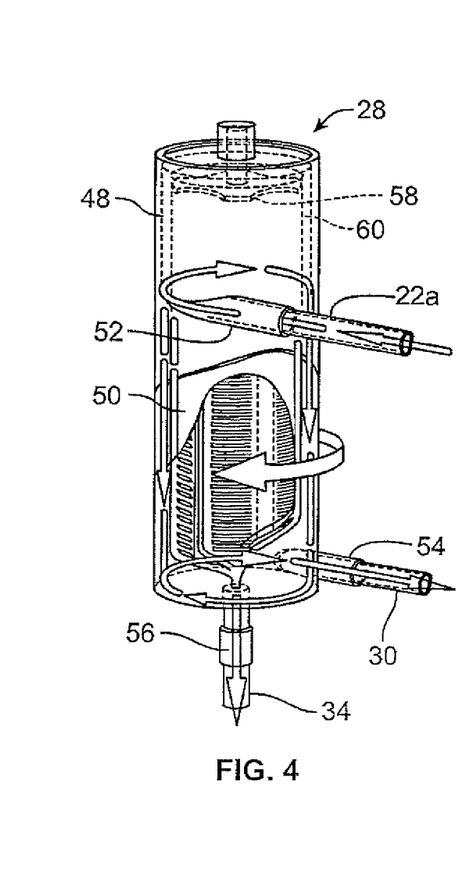
FIG. 4 is a front perspective view of a biological fluid (for example blood) separation chamber of the fluid flow circuit of FIG. 3, with a portion thereof broken away for illustrative purposes.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the return fluid away from the membrane 50 to exit the fluid separation chamber 28 via the side outlet 54, while the collection fluid passes through the membrane 50 toward the central axis of the housing 48 to exit the fluid separation chamber 28 via the bottom outlet 56. In one embodiment, whole blood from a blood source is separated into cellular blood components (return fluid) and substantially cell-free plasma (collection fluid). It should be understood that the present disclosure is not limited to a particular fluid separation chamber and that the illustrated and described fluid separation chamber 28 is merely exemplary. For example, in other embodiments, a differently configured spinning membrane-type fluid separation chamber may be employed (e.g., one in which the membrane 50 is mounted on an inside surface of the housing 48 or on both the rotor 58 and an inside surface of the housing 48 and facing the gap 60), or a centrifugal separation chamber or other design without departing from the scope of the present disclosure.

The illustrated membrane material may be formed into a sheet or film using any suitable techniques to define the membrane 50 that is to be mounted onto the rotor 58 of the fluid separation chamber 28. The dimensions and configuration of the membrane 50 may vary without departing from the scope of the present disclosure, but in one embodiment a membrane 50 such as described above, and used for separation of whole blood into plasma and cellular components may have a thickness in the range of approximately 5 μm to approximately 1000 μm (preferably in the range of approximately 25 μm to approximately 200 μm), with a mean pore size in the range of approximately 0.2 μm to approximately 200 (preferably in the range of approximately 0.5 μm to approximately 10 μm and more preferably in the range of approximately 0.6 μm to approximately 5 μm). The porosity of the membrane 50 may also vary, such as from approximately 1% to approximately 90%, but preferably in the range of approximately 50% to approximately 80% to produce a membrane 50 that passes fluid therethrough at a relatively high rate while being sufficiently strong to withstand the forces applied to it by the spinning rotor 58 and fluid contact during a separation procedure.

Figure 7:
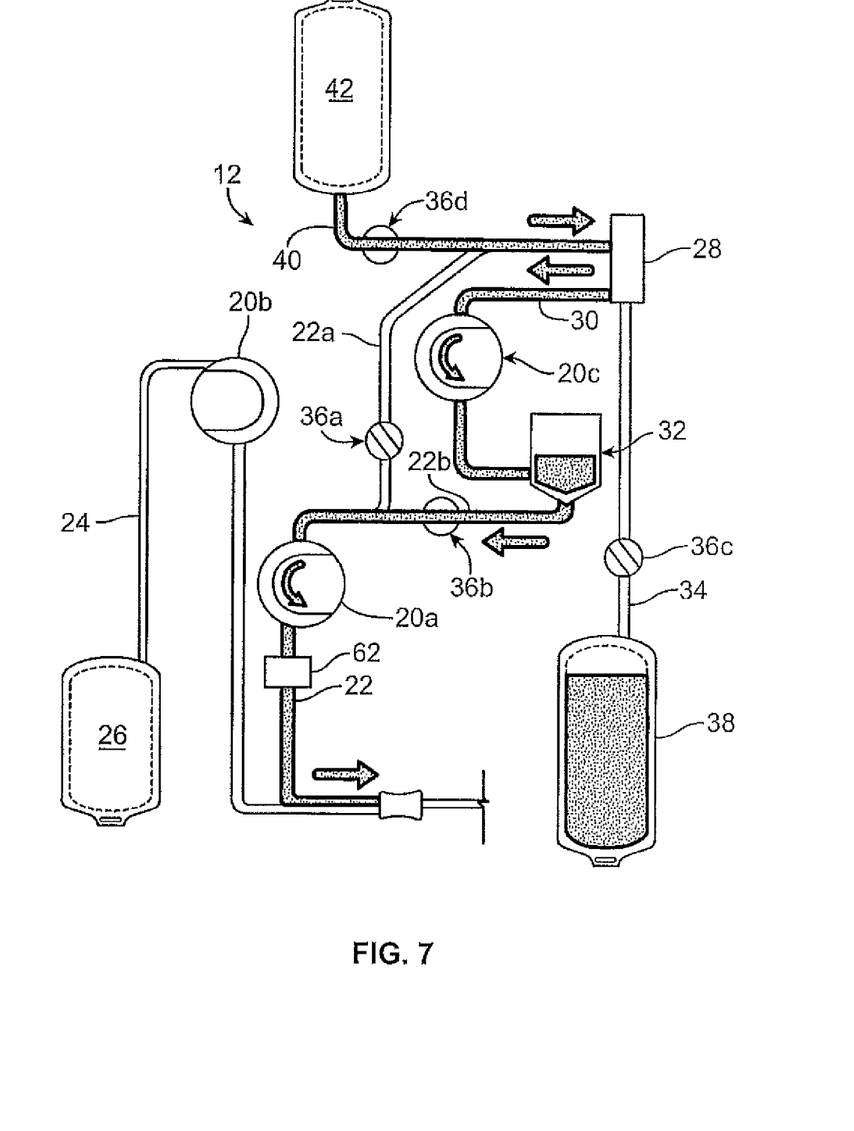
FIG. 7 is a schematic view of the fluid flow circuit and fluid separation system of FIG. 3, in a fluid return mode in which the return fluid is a replacement fluid, such a s saline.

According to one method of using the fluid separation system 10 and fluid flow circuit 12, a fluid is drawn from a fluid source into the fluid separation chamber 28, or a temporary holding chamber, during a draw phase or mode (FIG. 5), where it is separated into return fluid (e.g., cellular blood components) and collection fluid (e.g., substantially cell-free plasma). The collection fluid is retained by the system 10, while the return fluid is temporarily retained and returned to the fluid source during a return or infusion phase or mode (FIG. 6). FIG. 7 shows an exemplary phase or mode in which replacement fluid (e.g., saline) is directed to the fluid recipient, either alone or with an amount of return/processed fluid. In the phase of FIG. 7, the clamp or valve 36*d* associated with the replacement fluid line 40 is opened to allow replacement fluid to flow out of the replacement fluid source 42. The clamp or valve 36*a* associated with the draw branch 22*a* of the source/recipient access line 22 may be in a closed condition to prevent fluid flow therethrough, such that the replacement fluid is directed into the fluid separation chamber 28. The replacement fluid is pulled out of the fluid separation chamber 28 and into the return fluid reservoir 32 by operation of the pump 20*c* associated with the return fluid outlet line 30. If there is any return fluid in the return fluid reservoir 32, then the replacement fluid mixes with the return fluid prior to being pumped to the fluid recipient by the pump 20*a* associated with the fluid recipient line 22, otherwise the replacement fluid alone may be pumped to the fluid recipient. In one embodiment, the replacement fluid return mode of FIG. 7 is carried out only once, as a final return phase (e.g., when the amount of return fluid in the return fluid reservoir 32 is at a sufficiently low level) in which a mixture of return fluid and replacement fluid is returned to the fluid recipient. This may be advantageous to ensure that all of the return fluid in the return fluid reservoir 32 (along with any remaining in the fluid separation chamber 28) is rinsed out of the return fluid reservoir 32 and pumped to the fluid recipient.

In other embodiments, the replacement fluid return mode of FIG. 7 may be carried out at other times, such as earlier in the procedure, at multiple scheduled times during a procedure, and/or at any time upon a request from the operator and/or using a different path between the replacement fluid source 42 and the fluid recipient. For example, it may be advantageous for the replacement fluid to bypass the fluid separation chamber and the return fluid reservoir 32 if the replacement fluid is being pumped to a fluid recipient earlier in the procedure. In this case, the clamp or valve 36*d* associated with the replacement fluid line 40 and the clamp or valve 36*a* associated with the draw branch 22*a* of the source/recipient access line 22 may be opened to allow fluid flow therethrough, with the clamp or valve 36*b* associated with the reinfusion branch 22*b* in a closed condition to prevent fluid flow therethrough. The pump 20*a* associated with the fluid recipient line 22 may be activated (with the other two pumps 20*b* and 20*c* inactive) to draw replacement fluid out of the replacement fluid source 42 and through the replacement fluid line 40, the draw branch 22*a*, and finally the source/recipient access line 22 to the fluid recipient.

In one embodiment, the draw and return phases are repeatedly alternated (drawing from the fluid source, separating the fluid from the fluid source into return fluid and collection fluid, and then pumping the return fluid and/or a replacement fluid to the fluid source or a different recipient) until a target (e.g., a particular amount of collection fluid) is achieved. All of the draw phases and all of the return phases may be identical or may differ from each other. For example, a final draw phase may draw less fluid from the fluid source than the previous draw phases and a final return phase may infuse a combination of return fluid and replacement fluid to the fluid recipient, whereas the previous return phases pump might only return fluid to the fluid recipient.

Figure 8:
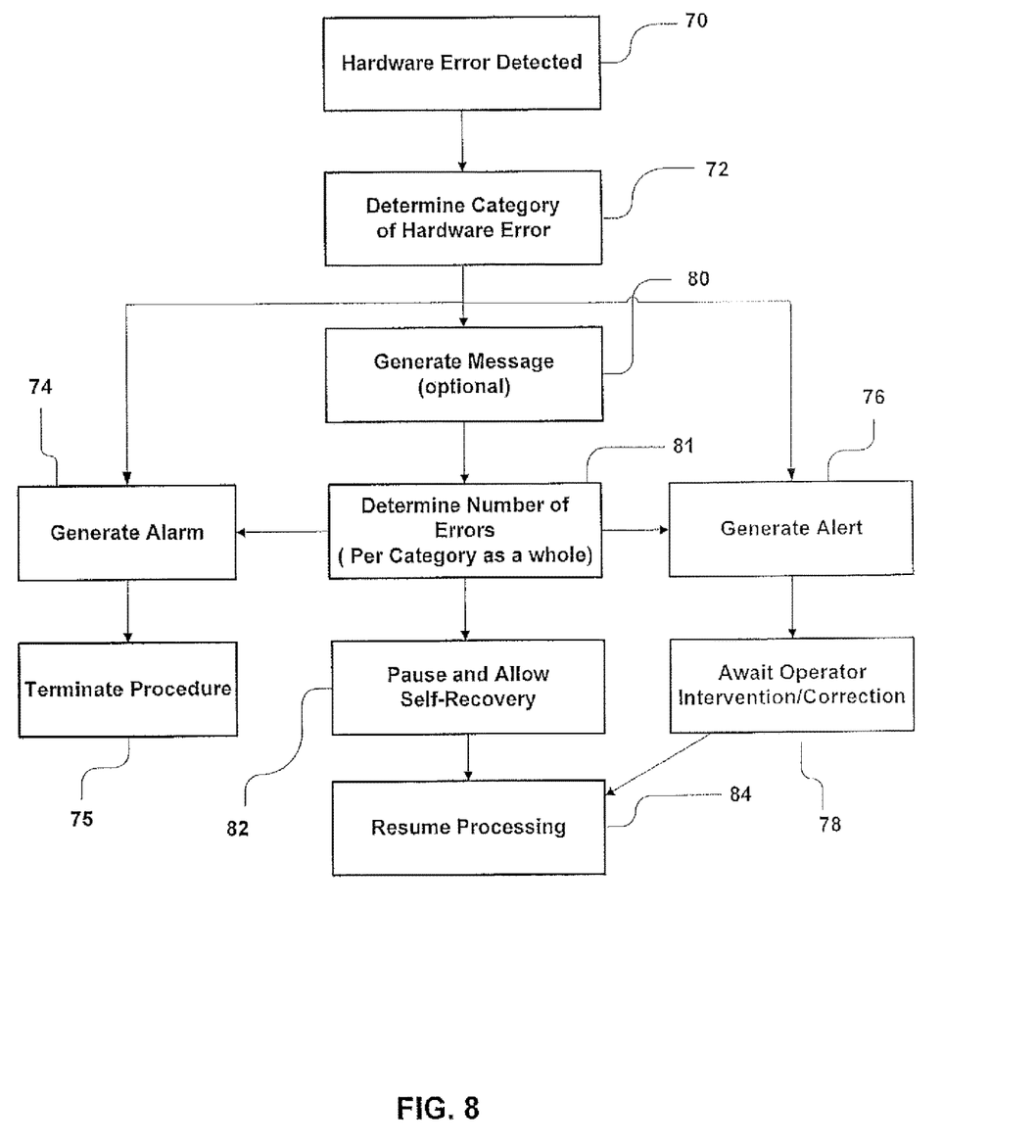
FIG. 8 is a flow chart depicting the various steps in the method carried out by the system in accordance with the present disclosure.

Systems of the type described above include several sensors/detectors that are built into hardware component 13 and communicate with the controller. Such sensors/detectors may detect the status of the procedure, conditions of the donor/patient, conditions within the fluid processing circuit 12 (e.g., pressure, flow rate), and errors in the hardware. As shown in FIG. 8, with regard to such hardware errors 70, they can range in severity and importance from those requiring termination of the procedure to those requiring intervention or acknowledgement by the operator to those that cannot be corrected but pose no harm to the safety of the donor or patient. In accordance with the present disclosure, the controller is pre-programmed to recognize the category of the hardware error (step 72). Depending on the category or type of hardware error detected, the controller then may automatically generate an alarm (step 74) requiring termination of the procedure (step 75). Alternatively, the controller may generate an alert (step 76) that may require intervention and/or acknowledgement (step 78) by the operator. Alerts and/or alarms may be graphical, textual, and/or audible.

In accordance with the present disclosure, the controller may also optionally generate a (graphical and/or textual) message shown in step 80 to the operator that an error that cannot be corrected but is otherwise of a category that poses no danger to the safety of the donor or patient has occurred. Examples of such hardware errors include and may include, without limitation pump and spinner rate errors (e.g., if the spinner is spinning too fast, too slow, is stalled, is not changing rates, is not stopping fast enough, or the direction of spin is reversed); clamps that do not open/close when intended; disturbances on the weight scales that increase signal variation/noise, but do not affect the average reading; inflation of the pressure cuff for a long period of time; readings of the pressure sensors that are outside of the normal range, but not hazardous; analog-to-digital conversions that did not complete as expected.

Once such error is detected, the system and the processing of the biological fluid may be paused temporarily for a selected period of time, as shown in step 82. The length of the pause may range anywhere between 0 seconds and 60 seconds. In a more particular embodiment, the length of the pause may be approximately 10 or fewer seconds. In any event, the pause should not be so long so as to add significant time to the processing procedure. The pause is not considered to be a termination of the procedure. As shown in FIG. 8, the pause at step 82 allows a period of time for the device to correct the error or otherwise self-recover. For pump and clamp errors, self-recovery may include one or more of the following steps: pulling power from the pumps, allowing the pumps to stop, restoring power to the pumps, and resuming the procedure/re-trying the previous procedure state. For pressure cuff errors, self-recovery includes deflation of the cuff, pausing of the procedure, and re-inflation the cuff. For weight scale errors, self-recovery includes stoppage of fluid flow into/out of the container on the scale and ensuring that no continued disturbance/noise or a change in the average reading is present. In the case of analog-to-digital conversion errors, the system pauses all hardware activities, reestablishes analog-to-digital conversion, and then resumes. In any event, processing of the biological fluid will resume, as shown in step 84.

In accordance with one embodiment of the present disclosure, system 10, and specifically the controller may keep track of such non-operator-correctable hardware errors of the type described above, as indicated in step 81. The controller may be pre-programmed such that if the number of non-operator-correctable hardware errors, either within a certain category of a non-operator-correctable error or all non-operator-correctable errors as whole reaches or exceeds a pre-selected value, the system may generate an alarm or alert in accordance with the protocol that requires termination of the procedure or operator intervention in response to more serious hardware errors, as described above and shown in steps 74 and 76, respectively.

Alternatively, if the number of non-operator-correctable hardware errors detected is less than the pre-selected value, the system may continue through the pause and self-recovery steps (82) and "resume processing" step (84), as described above relative to such errors.

Other Aspects

In a first aspect, a method of processing a biological fluid in an automated biological fluid processing system is provided. The system includes a hardware unit comprising a controller including pre-programmed instructions and a disposable fluid circuit mounted on said hardware unit. The method includes processing a biological fluid, detecting an error of a certain type and category in the hardware unit, pausing the processing, and resuming the processing without operator intervention.

A second aspect of the present subject matter includes the method in accordance with the first aspect including the steps of pausing the processing without terminating said processing.

A third aspect of the present subject matter includes the method in accordance with the second aspect including pausing said processing for less than 60 seconds.

A fourth aspect of the present subject matter includes the method in accordance with any one of the first and second aspects including processing blood to separate said blood into two or more components.

A fifth aspect of the present subject matter includes the method in accordance with any one of the first through third aspects including recognizing different types and categories of errors in the hardware unit.

A sixth aspect of the present subject matter includes the method in accordance with any one of the first through fifth aspects including correcting the error without operator intervention.

A seventh aspect of the present subject matter includes the method in accordance with any one of the first through fifth aspects including generating an alert or alarm when one or more errors in the hardware unit are detected and one or more of the errors are not corrected.

An eighth aspect of the present subject matter includes the method in accordance with the seventh aspect wherein said alert or alarm is an audible signal.

A ninth aspect of the present subject matter includes the method in accordance with any one of the first through eighth aspects wherein the alert or alarm is a graphical/textual message.

A tenth aspect of the present subject matter includes the method in accordance with any one of the first through ninth aspects wherein the error in the hardware unit is selected from the group consisting of pump and spinner rate errors; clamps that do not open/close when intended; disturbances on the weight scales that increase signal variation/noise; inflation of the pressure cuff for a long period of time; readings of the pressure sensors that are outside of the normal range, but not hazardous; analog-to-digital conversions that did not complete as expected.

An eleventh aspect of the present subject matter includes a system for processing a biological fluid comprising a biological fluid processor and a controller, wherein the controller includes pre-programmed instructions for performing the methods of any one of the first through tenth aspects.

In a twelfth aspect, a system for processing a biological fluid is provided. The system includes a reusable hardware unit including a controller including pre-programmed instructions to (i) detect errors in the hardware unit, (ii) recognize errors of varying types in the hardware unit, and (iii) allow processing of a biological fluid to continue without operator intervention. The system also includes a disposable fluid processing circuit mounted on the hardware unit.

A thirteenth aspect of the present subject matter includes the system of the twelfth aspect wherein the controller includes instructions to generate an alert in response to a detected error of a certain type in the hardware unit.

A fourteenth aspect of the present subject matter includes the system of the system of any one of the twelfth and thirteenth aspects wherein the controller is pre-programmed to pause a biological fluid processing procedure upon recognition of a certain type of error in the hardware unit.

A fifteenth aspect of the present subject matter includes the system of any one of the twelfth and fourteenth aspects wherein the controller is pre-programmed to record the occurrences of hardware errors.

A sixteenth aspect of the present subject matter includes the system of fifteenth aspect wherein the controller generates a message or alert when said controller records a pre-determined number of said hardware errors.

The invention claimed is:

1. A method of processing a biological fluid in an automated biological fluid processing system including a hardware unit comprising a controller including pre-programmed instructions and a disposable fluid circuit mounted on said hardware unit, the method comprising:
   a) processing a biological fluid;
   b) detecting a hardware error in the hardware unit;
   c) recognizing said hardware error as being of a certain category wherein said category comprises:
      i) a hardware error that generates an alarm and requires termination of said processing,
      ii) a hardware error that generates an alert and requires operator intervention and
      iii) a hardware error that cannot be corrected by the operator but that does not pose a danger to the patient or donor;
   d) pausing said processing when a hardware error of category (iii) is detected; and
   e) keeping track of a number of said category (iii) errors;
   f) comparing said number of such errors to a preselected number of errors to determine if the number of category (iii) errors exceeds said preselected number.

2. The method of claim 1 comprising pausing said processing without terminating said processing.

3. The method of claim 2 comprising pausing said processing for less than 60 seconds.

4. The method of claim 1 comprising processing blood to separate said blood into two or more components.

5. The method of claim 1 further comprising correcting said error without operator intervention.

6. The method of claim 1 further comprising generating an alert or alarm when one or more errors in said hardware unit are detected and one or more of said errors are not corrected.

7. The method of claim 6 wherein said alert or alarm comprises an audible signal.

8. The method of claim 1 wherein said alert or alarm comprises a graphical/textual message.

9. The method of claim 1 wherein said error in said hardware unit that cannot be corrected by the operator but poses no harm to the safety of a patient or donor error is selected from the group consisting of: pump and spinner rate errors; clamps that do not open/close when intended; disturbances on the weight scales that increase signal variation/noise; inflation of the pressure cuff for a long period of time; readings of the pressure sensors that are outside of the normal range, but not hazardous; analog-to-digital conversions that did not complete as expected.

10. A system for processing a biological fluid comprising a biological fluid processor and a controller, said controller including pre-programmed instructions for performing the method of claim 9.

11. The method of claim 1 comprising pausing said processing to allow for said hardware unit to self-recover.

12. The method of claim 11 wherein said hardware error comprises a pump error and said unit self-recovers by one or more of pulling power from a pump, allowing said pump to stop, restoring power to said pump.

13. The method of claim 11 wherein said hardware error comprises an analog to digital conversion that did not complete as expected and said unit self-recovers by re-establishing analog-to-digital conversion.

14. The method of claim 1 wherein said biological fluid is introduced into a rotating spinning membrane separator and wherein said hardware error comprises one or more of a spinner that is spinning too fast, a spinner that is spinning too slowly, a spinner that is stalled, a spinner that is not changing spinning rates, a spinner that is not stopping fast enough and a spinner wherein the direction of the spin is reversed.

15. A system for processing a biological fluid comprising:
a) a reusable hardware unit comprising a controller including pre-programmed instructions and is configured to:
1) detect hardware errors in said hardware unit;
2) recognize hardware errors of varying categories in said hardware unit wherein said categories include (i) a hardware error that generates an alarm and requires termination, (ii) a hardware error that generates an alert and requires operator intervention and (iii) a hardware error that cannot be corrected by the operator but that does not pose a danger to the patient or donor; and
3) keep track of and record a number of said category (iii) errors; and
4) compare said number of such category (iii) errors to a pre-selected number of such errors; and
5) allow processing of a biological fluid to continue without operator intervention if the number of said recorded errors does not exceed said pre-selected number of errors;
b) a disposable fluid processing circuit mounted on said hardware unit.

16. The system of claim 15 wherein said controller includes instructions to generate an alert or alarm in response to a detected error of a certain type in said hardware unit.

17. The system of claim 15 wherein said controller is pre-programmed and configured to pause a biological fluid processing procedure upon recognition of a certain type of error in said hardware unit.

18. The system of claim 17 wherein the certain type of error in said hardware unit is one that cannot be corrected by the operator but that does not pose a danger to the patient or donor.

* * * * *